United States Patent [19]

Price

[11] 4,119,404
[45] Oct. 10, 1978

[54] APPARATUS AND METHOD FOR SOUR GAS ANALYSIS

[75] Inventor: John G. W. Price, Carrollton, Tex.

[73] Assignee: Core Laboratories, Inc., Dallas, Tex.

[21] Appl. No.: 812,899

[22] Filed: Jul. 5, 1977

[51] Int. Cl.² ............................................. G01N 21/58
[52] U.S. Cl. ................................ 23/232 E; 23/232 R; 356/187; 422/89; 422/94
[58] Field of Search ............. 23/232 E, 232 R, 254 E, 23/254 R, 255 R; 356/87, 187

[56] References Cited

U.S. PATENT DOCUMENTS

| | | | |
|---|---|---|---|
| 3,423,181 | 1/1969 | Dimick et al. | 23/232 E X |
| 3,486,827 | 12/1969 | Binek et al. | 356/187 |
| 3,489,498 | 1/1970 | Brody et al. | 23/232 R X |

OTHER PUBLICATIONS

Brody et al., J. Gas Chromat. 4, 42 (1966).

Primary Examiner—Robert M. Reese
Attorney, Agent, or Firm—Lee C. Robinson, Jr.

[57] ABSTRACT

A flame photometric detector for use with a gas chromatograph comprises a burner to produce a cool hydrogen flame and excite molecules of the gas sample to emit light characteristic thereof, a transparent chimney surrounding the burner and flame to enhance characteristic light emission, a selective light filtering means, and sensing means positioned so as to exclude the flame from its sensing area. The device and method of operation are characterized by a substantially broader range of detection and measurement than is possible with present commercially available equipment.

16 Claims, 8 Drawing Figures

APPARATUS AND METHOD FOR SOUR GAS ANALYSIS

BACKGROUND OF THE INVENTION

Technological developments have significantly increased the demand for more reliable and versatile detection and measuring equipment. The detection and measurement of sulfur and sulfur bearing constituents are a prime concern for both technological and environmental reasons. A suitable device should give a specific, clear response to, and a rapid recovery from, all the volatile sulfur compounds in the gas sample. The device should further minimize interference from other constituents such as hydrocarbons. Measurements from the low ppm, (parts per million) range to a high pph (parts per hundred) range should be well within the detector's capabilities. The device should possess a low noise level, operational stability and sulfur response repeatability.

A special problem is presented by sour natural gas which may contain large amounts of hydrogen sulfide and comparatively smaller amounts of other sulfur bearing compounds such as carbonyl sulfide and lighter mercaptans. Generally, determination of the dilute components is frustrated because of the higher concentration contaminants, ultimately giving an unreliable analysis.

One commercially available unit is a phosphorus and sulfur specific flame photometric detector for use with a gas chromatograph. The device comprises a burner, a mirror and optical filters for the sulfur and phosphorous components, ignition plugs and a photomultiplier tube for each of the optical filtering devices. The device is characterized by alignment of the photomultiplier optical axis and survey area with the uppermost portion of the burner flame. Such positioning increases the sensing element's sensitivity to hydrocarbon presence and interferes with a clear reading specific to the sulfur and/or phosphorous content. Furthermore, the device has a limited operational range of from approximately 5 ppb (parts per billion) to 5 ppm (parts per million). "Sulfur saturation" severely limits the unit's reliable operational range and makes the apparatus undesirable for sour gas analysis.

SUMMARY OF THE INVENTION

The present invention, to a large extent, overcomes the difficiencies of the prior art devices. The invention is directed toward a detection-measurement device and related method characterized by good versatility and a wide operating range to produce highly reliable and accurate measurements of the constitutent being analyzed.

In a preferred embodiment, the device includes a burner having a relatively cool hydrogen flame which excites the molecules of a gas sample to produce characteristic light emissions. A transparent chimney surrounding the flame serves as a cooling chamber and concentrates the emissions in a preselected area. An optical filter allows only the characteristic wave lengths of the sulfur compounds to pass therethrough to a photo sensing device. The sensing device is so positioned as to exclude the burner flame from its optical sensing path, but include the area wherein the light emissions have been concentrated. Such positioning effectively eliminates flame noise and hydrocarbon interference from the sensing path of the photo sensing device. A recordable and measurable signal is generated and the same transmitted to a display or readout station.

The various features of novelty which characterize the invention are pointed out with particularity in the claims annexed to and forming a part of the specification. For a better understanding of the invention, its operating advantages and specific objects obtained by its use, reference should be had to the accompanying drawings and the descriptive matter in which there is illustrated and described a preferred embodiment of the invention.

DESCRIPTION OF A PREFERRED EMBODIMENT

The present invention generally relates to a method and apparatus for detection and measurement of sulfur and sulfur bearing compounds, and is more specifically directed at the detection and measurement of sulfur and sulfur bearing compounds in sour natural gas samples.

Figure 1:
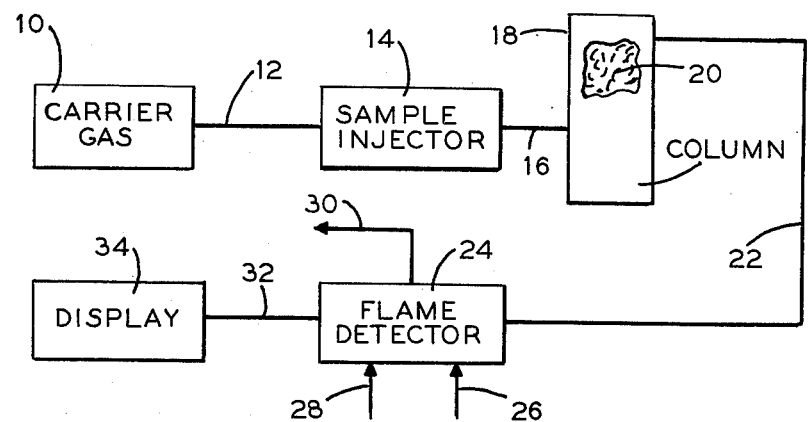
FIG. 1 generally depicts the use of the present invention with a gas chromatograph.

Referring to FIG. 1, an inert carrier gas 10, such as nitrogen, entrains a sample of the gas to be analyzed in a sample injector 14. The carrier gas is piped to and from the injector 14 by lines 12 and 16 respectively. Line 16 feeds into chromatograph column 18 wherein a physical separation of the sample's gaseous components, based on their respective partition coefficients, is carried out. The separation process is basically an adsorption process with the less mobile components of the gaseous sample (stationary phase) being physically bound to the column packing 20. In the present embodiment, the column is inert to sulfur compounds which are contained in the mobile phase. The latter phase, still entrained by the carrier gas, is not detained by the packing but flows from the column via line 22 and continues to the detection unit 24 wherein it mixes with hydrogen fuel stream 26. Combustion sustaining gas stream 28 is introduced into the detector and ultimately produces combustion products which are exhausted from the detector via line 30. Unit 24 produces a recordable and measurable signal which is transmitted to display 34 by output or lead 32.

Figure 2:
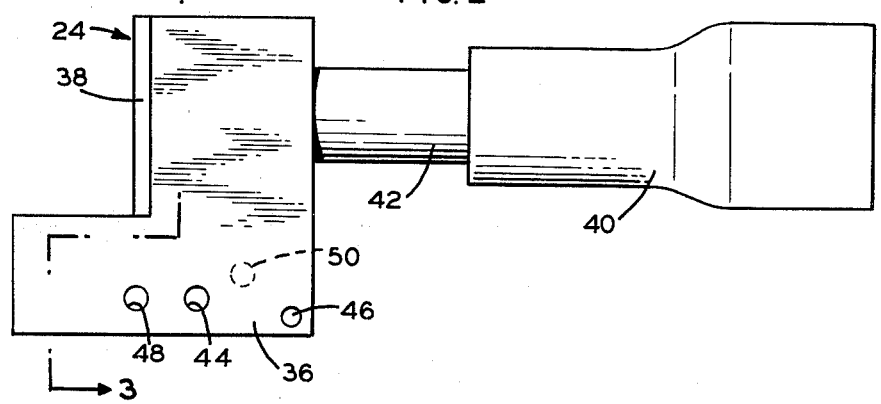
FIG. 2 is a side view of the flame detector of FIG. 1.

Referring to FIG. 2, flame detector 24 comprises a detector block 36 with an inspection plate 38. Block 36 is connected to a photomultiplier tube 40 by light tube 42. Light tube 42 houses an optical filter (FIG. 4) and accessory devices such as secondary filters (not shown) and condensing lenses (not shown). The light tube may be operated with a slightly pressurized gas to clear the tube of scattering or absorbing substances and dissipate undesirable levels of heat. Lead 32 feeds the signal generated by the tube 40 to display 34 (FIG. 1). Hydrogen fuel is introduced into block 36 through port 44. A thermocouple (not shown), which allows continuous monitoring of detector block temperature, is inserted in port 46. Port 48 is for insertion of an electrically operated heater cartridge capable of producing an operating temperature of 300° C. (572° F.). Port 50 (shown in phantom) is for introduction of the combustion sustaining gas into the block.

Figure 3:
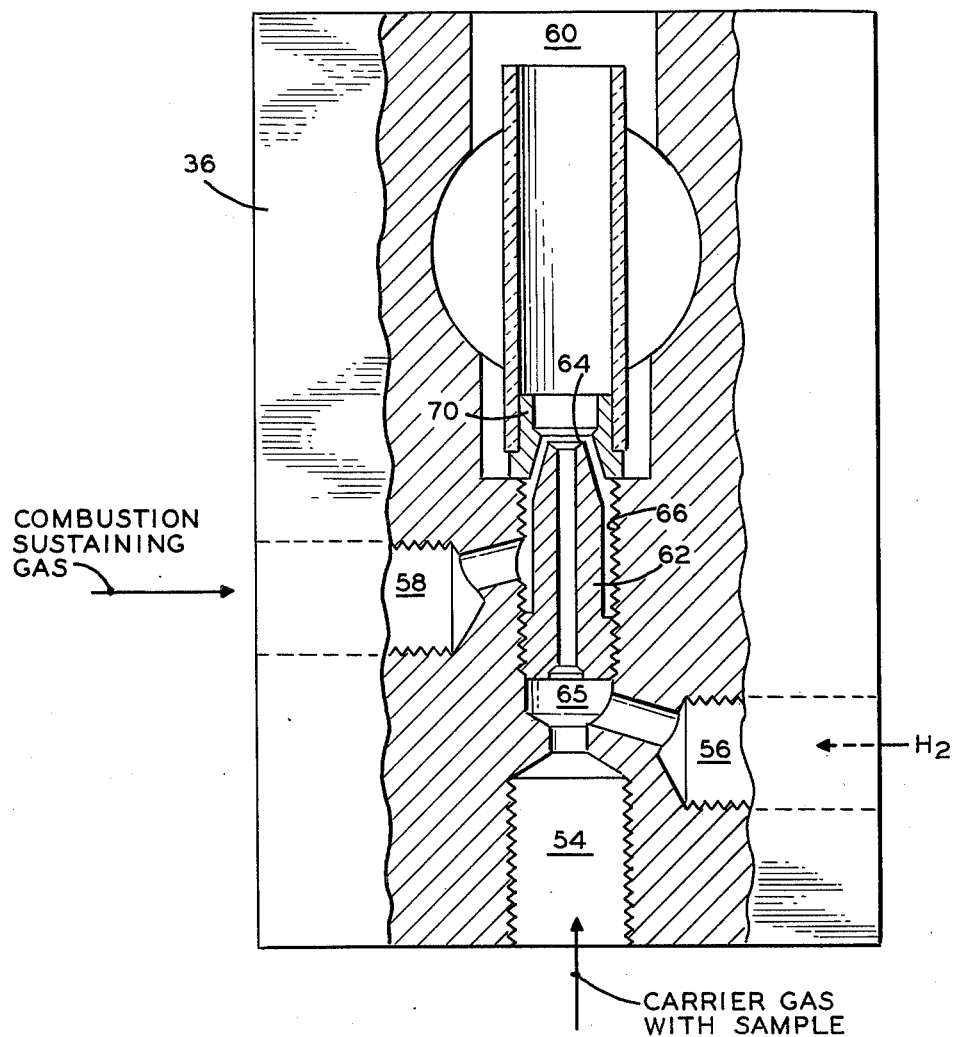
FIG. 3 is a section taken along line 3—3 in FIG. 2.

FIG. 3 depicts block 36 in cutaway. Block 36 is formed with cavities 54, 56, 58 and 60. Cavity 54 extends from port 52 and is used for introducing the gas sample from column 18 into burner or flame tip 62. The burner or flame tip is preferably made of a high nickel alloy or other material relatively unreactive with sulfur. Cavity 56 extends from port 44 and leads the hydrogen fuel to burner 62. A combustion sustaining gas, such as air or oxygen, enters block 36 through port 50 and flows through cavity 58 to an annular gas chamber 66 which surrounds the burner. This gas then feeds into cavity 60 to support combustion of the hydrogen and gas sample. A transparent chimney 68 surrounds flame tip 64 and is held in position by support ring 70. The chimney is constructed of transparent material which is preferably quartz or a laboratory grade glass such as Pyrex. The chimney extends a preselected distance above the uppermost portion of the flame tip and is critical to substantially improved performance of the unit.

Figure 4:
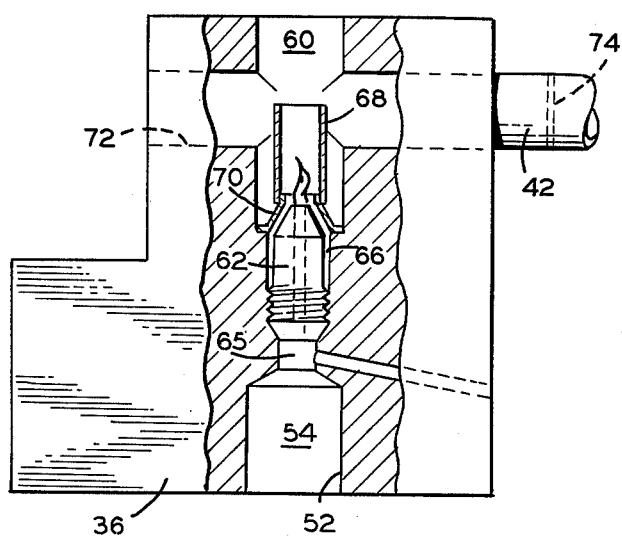
FIG. 4 shows a cut away view of the detector of FIG. 2.

Referring to FIG. 4, block 36 is formed with an enlarged bore 72 transversing cavity 60. One end of the bore is used for access to the cavity and when not being so used is closed off by inspection plate 38 (FIG. 2). The bore's opposite end is attached to the photomultiplier tube 40 by the tightly sealed light tube 42. Light tube 42 houses selective optical filter 74. The light tube is critically positioned so that the line of sight of the sensing unit or its sensing area does not include any portion of the cool hydrogen flame. The optical filter is selective and allows only particular emissions to pass therethrough thus minimizing hydrocarbon interference.

The analyzer, having received the carrier gas and mobile phase from the chromatograph column operates in the following manner. The hydrogen fuel and gas sample are mixed in the lower burner mixing area 65 and ignited by any conventional ignition arrangement. Combustion sustainig gas flows through the annular chamber 66 surrounding the burner and combusts with the hydrogen-sample gas mixture to produce a cool hydrogen flame. Such an arrangement improves operational stability. The flame temperature lies within the 300° C.-800° C. (572° F.-1472° F.) range rather than the 2300° C. (4172° F.) temperature of a common type of commercially available flame detection unit. The hydrogen to combustion gas (air) ratio and the hydrogen-carrier gas ratio are of the order of 3:1 and 5-8:1, respectively. In cases in which oxygen is used as the combustion gas, the hydrogen to oxygen ratio is about 15:1. The cumulative effect of these selected flow ratios significantly contributes to producing the cool flame and clean flow effect and compares favorably with the prior art fuel to combustion gas ratio of 2:3. The clean flow effect is the most significant factor contributing to the detector's rapid response to the sulfur bearing constituents. The relatively cool hydrogen flame significantly enhances formation of $S_2$ molecules in a high energy state which produces the characteristic light emission at the 394nm wave length (1 nm = 0.000000001 meters) upon decay to a lower energy state. Evidence indicates that low energy $S_2$ molecules absorb 394 nm light producing an undesirable quenching effect on the properly excited molecules. The high flow rate carrier gas, besides contributing to the cooling effect of the flame, sweeps spent $S_2$ molecules (low level energy) from the detection device.

Transparent chimney 68, which surrounds the uppermost section of the burner and the entire flame, functions as a contact type heat exchanger to cool the excited $S_2$ molecules to a lower energy state where the 394 nm light emissions occur. The chimney further serves to concentrate maximum emission of the light into a specific area above the hydrogen flame in full view of the sensing unit scan area. This particular enfiguration is credited with giving a 400-500% more specific response to sulfur than prior art units. Detector dead volume, which represents areas of stagnation of the decaying molecules, is significantly reduced by the presence and operation of the chimney device. This reduction is credited with the definite and sharp signal peak produced by the inventive detector. Where polar and highly reactive species such as sulfur compounds are being analyzed, the chimney isolates such species from being adsorbed on or chemically reacting with surrounding metal surfaces. Interreaction of any type with metal housing can seriously impair the analyzer's reliability. Dimensional characteristics of the chimney are important for it to efficiently and effectively function in the multipurpose manner above described. For the common analytical instrument burner, the chimney should have an inner diameter of 0.75 centimeters (0.34 inches) and extend 3 centimeters (1.35 inches) above the burner or flame tip. Variation from these dimensions leads to flame blow out and inefficient cooling of the over excited $S_2$ molecules.

The concentrated light emissions of the properly excited $S_2$ molecules are selectively allowed to pass through filter 74 in light tube 42. Filter 74 may be of a type which allows a number of varied wave lengths to pass, or it may be a narrow band pass filter specific for the 394 nm wave length. The latter type filter effectively filters out most other signals. The selectively filtered emissions pass through the light tube to the photomultiplier where, based on the intensity of the emissions, an electrical signal is generated and amplified or merely generated and transmitted to a recording or a display panel.

Figure 5:
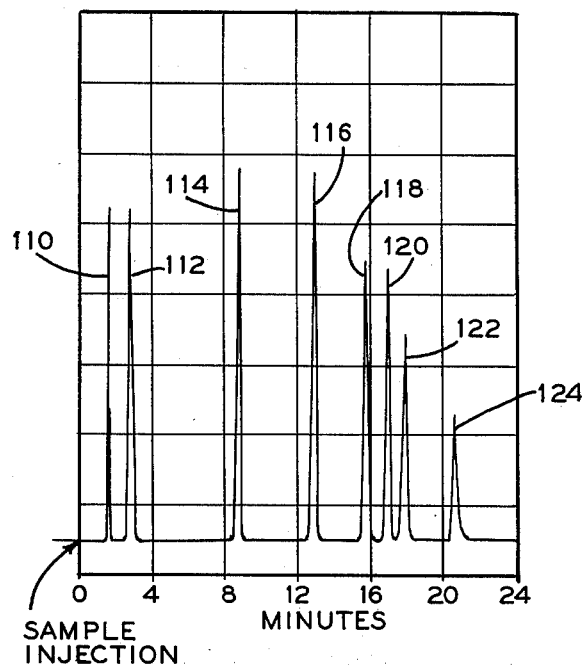
FIG. 5 is a scan of test results obtained using the present invention to analyze a calibration gas.
Figure 6:
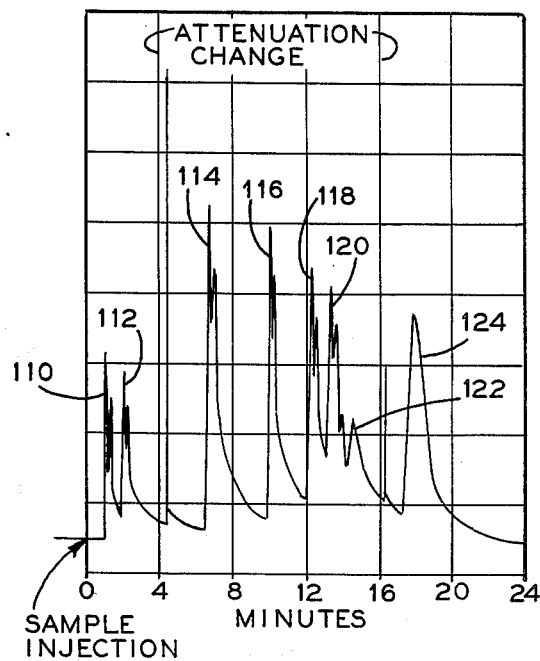
FIG. 6 is a scan of test results obtained using a prior art device to analyze calibration gas.

Comparative testing of the present invention with prior art devices indicates superior performance over commercially available units. Referring to FIGS. 5 and 6, a calibration gas containing 0.5% of each of the following sulfur components was used to test and compare the present invention with a prior art device.

| COMPONENT | REFERENCE NUMERAL |
|---|---|
| Hydrogen Sulfide ($H_2S$) | 110 |
| Carbonyl Sulfide (COS) | 112 |
| Methyl Mercaptan ($CH_3SH$) | 114 |
| Ethyl Mercaptan ($CH_5SH$) | 116 |
| Isopropyl Mercaptan ($C_3H_7SH$) | 118 |
| n-Propyl Mercaptan ($C_3H_7SH$) | 120 |
| t-Butyl Mercaptan ($C_4H_9SH$) | 122 |
| n-Butyl Mercaptan ($C_4H_9SH$) | 124 |
| i-Butyl Mercaptan ($C_4H_9SH$) | 126 |

Figure 7:
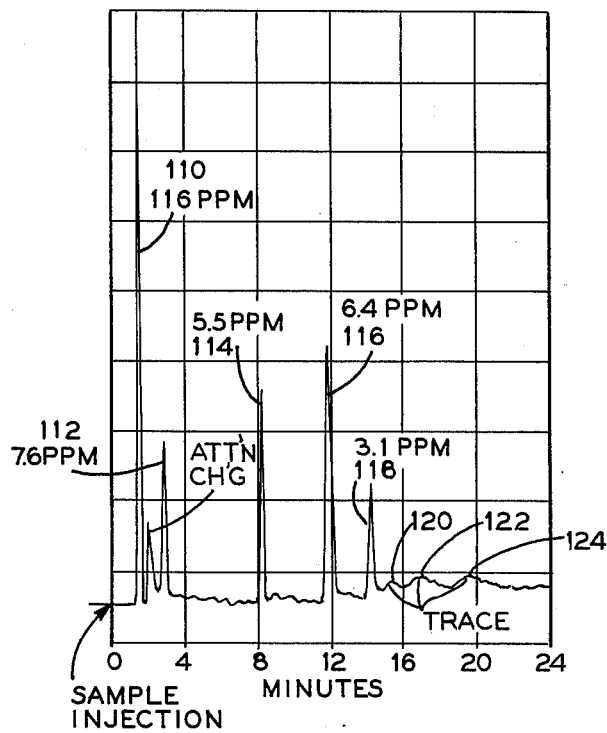
FIG. 7 is a scan of test results from the present invention using a low sulfur sample.
Figure 8:
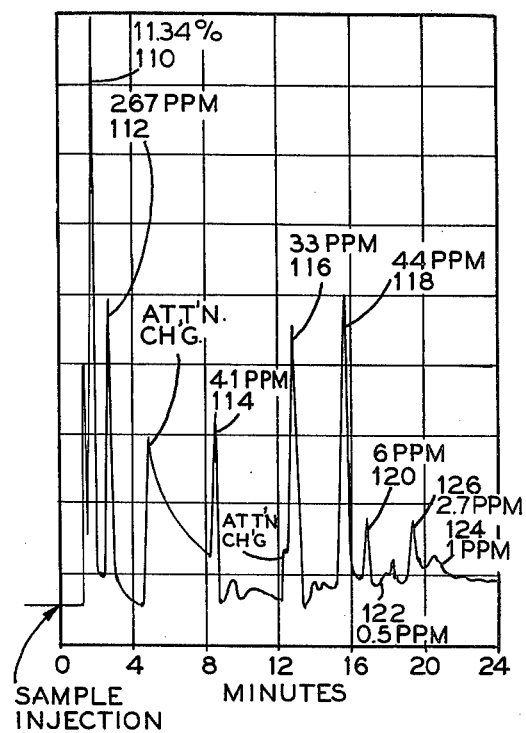
FIG. 8 is a scan of test results from the present invention using a high sulfur sample.

The respective detector scans clearly indicate that the present invention produced a more accurate and more specifically defined sample analysis than was produced by the prior art device. Furthermore, the present invention did not produce folding or tailing peaks which are indications of saturation and erratic unit performance. FIGS. 7 and 8 show the invention-detector's performance on gas samples containing 116 ppm and 113,000 ppm of $H_2S$ respectively. The gas samples also contained low concentrations of the other sulfur containing compounds listed and numbered as above. While attenuation adjustments were periodically needed with the higher concentration samples, reliably accurate results were obtained. The prior art device could not analyze the samples used for the data displayed in FIGS. 7 and 8.

The present invention has also been found useful for analysis of sour natural gas samples and LPG fractions of petroleum. The device can detect a wide variety of sulfur bearing constituents in quantities from about 0.1 ppm up to and in excess of 5000 ppm. Specifically, in addition to those listed above, the device can be used for determination of sulfur dioxide ($SO_2$), carbon disulfide ($CS_2$) dimethylsulfide ($C_2H_6S$), ethylmethylsulfide ($C_3H_8S$), s-butyl, or i-butyl mercaptans ($C_4H_9SH$), and diethylsulfide ($C_4H_{10}S$).

As used herein the term "light" includes not only visible light but also radiation having wavelengths longer and shorter than the visible spectrum.

The terms and expressions which have been employed are used as terms of description and not of limitation, and there is no intention in the use of such terms and expressions of excluding any equivalents of the features shown and described or portions thereof, it being recognized that various modifications are possible in the scope of the invention.

What is claimed is:

1. A flame photometric detector comprising a burner means with a tip; means for supplying to the burner a gas sample for analysis and a fuel; means for supplying combustion supporting gas to the burner tip; means to produce a flame to excite constituents of the sample and produce characteristic light emissions thereof; an elongated transparent chimney surrounding the flame to cool the excited constituents and concentrate maximum light emission in a preselected area remote from and excluding the flame; optical filtering means to allow only preselected characteristic light emissions to pass therethrough; and photo detector means having an optical sensing path which includes the preselected area of emission concentration but excludes the flame, and detects the emissions passing through the filtering means to produce at least one signal.

2. In combination with the detector of claim 1, recording means for recording the least one signal.

3. In combination with the detector of claim 1, chromatographic means for conditioning the gas sample before its introduction into the detector.

4. The detector of claim 1 wherein the chimney is glass.

5. A sulfur specific flame photometric detector comprising a burner means with a sulfur resistant tip; means to supply a mixture of fuel and gas sample thereto; means to separately supply a combustion supporting gas directly to the burner tip; means to produce a flame to excite sulfur bearing molecules of the gas sample and produce characteristic light emissions thereof; means to concentrate light emissions in a preselected area remote from and excluding the flame; optical filtering means to allow only preselected characteristic light emissions to pass therethrough; and photo detector means having an optical sensing path, which includes the preselected area of emission concentration but excludes all portions of the flame and detects the emissions passing though the filtering means to produce at least one signal.

6. A method for detection and measurement of sulfur constituents in a gas sample comprising: maintaining a cool flame having a temperature below about 800° C.; introducing the gas sample into said cool flame to excite molecules of components of the sample and produce light emissions characteristic thereof; concentrating the light emissions in a predetermined area remote for the cool flame; filtering the light emissions to pass preselected light emissions; sensing the light emissions in the predetermined area to produce a signal; and recording the signal.

7. The method of claim 6 wherein the sulfur constituents include sulfur bearing hydrocarbons.

8. The method of claim 6 wherein the light emissions are filtered to pass a preselected light emission.

9. The method of claim 6 wherein the cool flame is produced by a high hydrogen fuel to air mixture and a high carrier gas flow rate, the hydrogen fuel to air ratio in said mixture being at least about 3 to 1.

10. The method of claim 6 for detection and measurement of sulfur constituents of LPG fraction of petroleum.

11. The method of claim 6 wherein the sensed sulfur constituents each comprise from trace amounts to 5,000 ppm of the gas sample.

12. The method of claim 11 wherein the sulfur constituents include sulfur bearing hydrocarbons.

13. An apparatus for analyzing a sample to detect and measure the sulfur content thereof comprising: a flame tip with means for mixing and leading thereto a mixture of fuel and gas sample; an annular chamber surrounding the flame tip for introduction of a combustion sustaining gas to the flame; means for producing a flame at the flame tip to produce characteristic light emissions from the gas sample; chimney means surrounding the flame tip to cool the flame and concentrate the light emissions in a preselected area remote from the flame; means for exhausting gaseous components from the apparatus; filtering means to pass selected light emissions therethrough, sensing means having an optical path which includes the preselected area remote from the flame but excludes the flame; signal generation means operating in response to the sensing means; recording and measurement means functioning in response to the signal generation means.

14. A method for detection and measurement of sulfur constituents in a gas sample comprising: maintaining a cool flame having a temperature below about 800° C.; introducing the gas sample into said cool flame to excite molecules of components of the sample and produce light emissions characteristic thereof; concentrating the light emissions in a predetermined area remote from the cool flame; filtering light emissions to pass preselected light emissions; sensing the light emissions in the predetermined area to produce a signal; sweeping spent molecules from the predetermined area; and recording the signal.

15. A method for detection and measurement of sulfur constituents in a gas sample wherein the sulfur constituents comprise at least 0.1 ppm of the sample, the method comprising: introducing the gas sample into a cool flame to excite molecules of components of the sample and produce light emissions characteristic thereof; concentrating the light emissions in a predetermined area remote from the cool flame; filtering the light emissions to pass preselected light emissions; sensing the light emissions in the predetermined area to produce a signal corresponding to sulfur constituents from about 0.1 ppm of the sample to about 5,000 ppm of the sample; sweeping spent molecules from said predetermined area; and recording the signal.

16. A method for detection and measurement of sulfur constituents of sour natural gas comprising: maintaining a cool flame by burning a mixture of hydrogen and combustion sustaining gas, the hydrogen to combustion sustaining gas ratio in said mixture being at least about 3 to 1; introducing a sample of the sour natural gas into said cool flame to excite molecules of components of the sample and produce light emissions characteristic thereof; concentrating the light emissions in a predetermined area remote from the cool flame; filtering the light emissions to pass preselected light emissions; sweeping spent molecules from the predetermined area; sensing the light emissions in the predetermined area to produce a signal; and recording the signal.

* * * * *